United States Patent [19]

Ono et al.

[11] 4,053,625
[45] Oct. 11, 1977

[54] INSECTICIDES

[75] Inventors: Isao Ono, Kawanishi; Yoshitoshi Okuno, Toyonaka; Toshio Nishioka, Takarazuka; Nobushige Itaya, Nishinomiya, all of Japan

[73] Assignee: Sumitomo Chemical Company, Limited, Osaka, Japan

[21] Appl. No.: 634,850

[22] Filed: Nov. 24, 1975

[30] Foreign Application Priority Data

Dec. 5, 1974 Japan .................... 49-140657

[51] Int. Cl.² ............................ A01N 9/22
[52] U.S. Cl. .................... 424/274; 260/326.43
[58] Field of Search .......... 260/326 NS, 326.43; 424/274

[56] References Cited
U.S. PATENT DOCUMENTS

| 3,428,651 | 2/1969 | Kato et al. | 260/326.43 |
| 3,766,218 | 10/1973 | Ueda et al. | 260/326 NS |
| 3,934,023 | 1/1976 | Okuno et al. | 424/274 |
| 3,954,814 | 5/1976 | Mizutani et al. | 260/326 NS |

FOREIGN PATENT DOCUMENTS

| 2,185,612 | 4/1974 | France | 260/326 NS |

*Primary Examiner*—Ethel G. Love
*Attorney, Agent, or Firm*—Stevens, Davis, Miller & Mosher

[57] ABSTRACT

A cyclopropanecarboxylic acid ester of the formula (I), (I)

-continued $$R_3\text{-ring}(C=O, C=O)N-CH_2OC(O)-CH-CH-CH=C(R_1)R_2 \text{ with } C(CH_3)(CH_3) \text{ cyclopropane}$$

wherein $R_1$ is a hydrogen atom, methyl group or a fluorine, chlorine or bromine atom, $R_2$ is a fluorine, chlorine or bromine atom, and each of $R_3$ and $R_4$ is independently a hydrogen atom, a $C_1$–$C_3$ alkyl, $C_2$–$C_3$ alkenyl or $C_2$–$C_3$ alkynyl group, an alkyl- or halogen-substituted aryl, unsubstituted aryl group or an aralkyl group, which possesses various useful insecticidal and acaricidal activities and can be prepared by reacting an alcohol, halide or arylsulfonate compound of the formula (II), (II)

$$R_3\text{-ring}(C=O, C=O)N-CH_2-A$$

wherein $R_3$ and $R_4$ have the same meanings as defined above and A is a hydroxyl group, a halogen atom or an arylsulfoxy group, with a cyclopropanecarboxylic acid of the formula (III), (III)

$$HO-C(O)-CH-CH-CH=C(R_1)R_2 \text{ with } C(CH_3)(CH_3) \text{ cyclopropane}$$

wherein $R_1$ and $R_2$ have the same meanings as defined above, or its reactive derivative.

9 Claims, No Drawings

INSECTICIDES

The present invention relates to a novel cyclopropanecarboxylic acid ester of the formula (I),

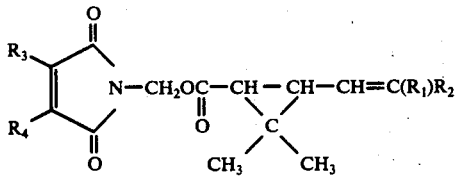
(I)

wherein $R_1$ is a hydrogen atom, methyl group or a fluorine, chlorine or bromine atom, $R_2$ is a fluorine, chlorine or bromine atom, and each of $R_3$ and $R_4$ is independently a hydrogen atom, a $C_1$-$C_3$ alkyl, $C_2$-$C_3$ alkenyl or $C_2$-$C_3$ alkynyl group, an alkyl- or halogen-substituted $C_6$-$C_8$ aryl, unsubstituted $C_6$-$C_8$ aryl group or a $C_7$-$C_9$ aralkyl group, which is useful as an insecticide and an acaricide. An object of the present invention is to provide insecticides and acaricides, at a low cost, which exhibit low toxicity to mammals but have a strong insecticidal activity and a rapid effect, for use in agriculture and horticulture as well as public health.

Among the insecticides, pyrethrum extracts (containing pyrethrin) and synthetic allethrin which is a homologue of the active ingredient of said extracts are known and have been widely used for the control of harmful insects because of their rapid effect upon insects and low toxicity to mammals. However, the pyrethrum extracts tend to be limited in use owing to the relatively high cost in spite of the excellent usefulness.

The inventors synthesized various cyclopropanecarboxylic acid esters and tested the biological activity thereof. As the result, it was found that the present esters of the formula (I) have an excellent knock-down effect and insecticidal activity against sanitary insects such as houseflies and the like, particularly against insects injurious to agriculture such as green rice leafhoppers, diamond-back moths, armyworms, cutworms and the like, and further a repellency to mites which are parasitic on animals and plants. The inventors further found that the present esters exhibit low toxicity to mammals and can be prepared at a low cost.

The esters of the present invention can be widely used for public health, and further they have a strong insecticidal activity against insects injurious to stored cereals, agriculture or forestry, and against mites which are parasitic on animals. Therefore they are very useful for controlling these insects. Particularly, they are so low in toxicity to mammals that they can be used for agricultural crops before harvest, greenhouse cultivation, household horticulture and food-packaging.

The novel cyclopropanecarboxylic acid ester of the formula (I) can be obtained by reacting an alcohol, halide or arylsulfonate, of the formula (II),

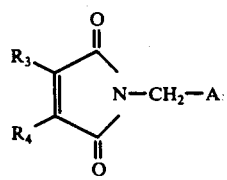
(II)

wherein $R_3$ and $R_4$ are as defined above, and A is a hydroxyl group, a halogen atom, or an arylsulfoxy group with a cyclopropanecarboxylic acid of the formula (III),

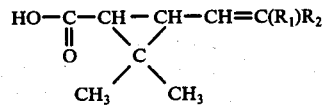
(III)

wherein $R_1$ and $R_2$ are as defined above, or its reactive derivative, optionally in the presence of a suitable solvent, reaction assistant or catalyst.

The above mentioned reactive derivatives of the cyclopropanecarboxylic acid may be an acid halide, acid anhydride, alkali metal salt thereof, organic tertiary amine salt thereof and the like.

The esters of the formula (I) have geometrical isomers due to the stereo structure of the carboxylic acid (III) and optical isomers due to the asymmetric carbon atoms of the carboxylic acid (III), and all of these isomers are within the scope of the present invention.

Methods for the preparation of the present compounds of the formula (I) will be illustrated in more detail below.

The first embodiment is a method which comprises reacting an alcohol of the formula (II) with a carboxylic acid of the formula (III) or its acid halide or acid anhydride.

When the carboxylic acid itself is used, the reaction is carried out under conditions which promote dehydration. Thus, the alcohol can be reacted with the carboxylic acid at room temperature or under heating, in a suitable inert solvent such as benzene or petroleum ether in the presence of a dehydrating agent such as dicyclohexylcarbodiimide.

When a carboxylic acid halide is used, the reaction is sufficiently accomplished at room temperature by reacting the alcohol with the acid halide using as a hydrogen halide acceptor, for example, an organic tertiary base, e.g. pyridine or triethylamine. The acid halide used in this case may optionally be selected within the range of the present invention, but is preferably an acid chloride. In this reaction, the presence of a solvent is desirable for smooth progress of the reaction and an inert solvent such as benzene, toluene, petroleum ether or the like is usually used.

When the carboxylic acid anhydride is used, the reaction can be achieved by reacting the alcohol with the acid anhydride at room temperature and no particular reaction assistant is required. In this case, heating of the reaction system and the use of an inert solvent are desirable for smooth progress of the reaction, but they are not essential.

The second embodiment is a method for obtaining an ester of the formula (I) using a compound which is obtained by substituting the hydroxyl group of the alcohol of formula (II) with a halogen atom. The halogen atom used herein is a chlorine or bromine atom in general but other halogen atoms can also be selected optionally. The carboxylic acid of the formula (III) which is the another compound of the reaction is used in the form of an alkali metal salt or an organic tertiary base salt. Alternatively, a base which can form these salts may be added to the reaction system together with the carboxylic acid. In this case, it is desirable for performance of the reaction to use a suitable inert solvent such as benzene and acetone and to heat reaction system at the boiling point of the solvent used or lower temperature.

The third embodiment is a method for obtaining an ester of the formula (I) using a compound which is obtained by substituting the hydroxyl group of the alcohol or formula (II) with an arylsulfoxy group. The another compound and the reaction condition used herein are the same as described in the second embodiment of the invention.

The compound which is obtained by substituting the hydroxyl group of the alcohol of the formula (II) with a halogen atom or an arylsulfoxy group is easily prepared by halogenating the alcohol of formula (II), or by reacting the alcohol of formula (II) with p-toluenesulfonic acid chloride or the like.

The methods for the production of the compounds of the present invention will be illustrated with reference to the following examples. The esters of the present invention in the following Table were produced by standard procedures each represented by A, B, C, D, and E as follows.

Method A: The reaction between an alcohol of the formula (II) and a carboxylic acid halide An alcohol (0.05 mole) is dissolved in three times its volume of dry benzene and 0.075 mole of pyridine is added to the solution. Separately, 0.053 mole of a carboxylic acid chloride is dissolved in three times its volume of dry benzene and the resulting solution is added at one time to the former solution. The reaction proceeds under generation of heat. The reaction mixture is allowed to stand overnight in a tightly sealed vessel. Thereafter, a small amount of water is added thereto to dissolve pyridine hydrochloride deposited and the aqueous layer is separated. The organic layer obtained is washed successively with a 5% aqueous hydrochloric acid solution, an aqueous solution saturated with sodium hydrogen carbonate and then a saturated aqueous solution of sodium chloride. After drying over anhydrous sodium sulfate, the benzene is removed under reduced pressure and the residue obtained is purified by chromatography on silica gel to obtain the objective ester.

Method B: The dehydration reaction between an alcohol of the formula (II) and a carboxylic acid of the formula (III)

An alcohol (0.05 mole) and a carboxylic acid (0.05 mole) are dissolved in three times its volume of 30 benzene. To the solution is added 0.08 mole of dicyclohexylcarbodiimide, and the mixture is allowed to stand overnight in a tightly sealed vessel, then refluxed for two hours to complete the reaction and then subjected to the same after-treatment as described in the standard Method A to obtain the objective compound.

Method C: The reaction between an alcohol of the formula (II) and a carboxylic acid anhydride An alcohol (0.05 mole) is dissolved in three times its volume of toluene and 0.05 mole of a carboxylic acid anhydride (prepared from the carboxylic acid and acetic anhydride) is added thereto. The mixture is reacted at 100° C for 3 hours under heating and then cooled. The reaction mixture is neutralized with a 10% aqueous solution of sodium hydroxide at a temperature lower than 10° C and the carboxylic acid resulting from the reaction is recovered as the sodium salt thereof from the aqueous layer. The organic layer is treated by the same manner as that described in the standard Method A to obtain the objective ester.

Method D: The reaction between a halogenated methyl compound of the formula (II) and the carboxylic acid of the formula (III)

A halogenated methyl compound (0.05 mole) and a carboxylic acid (0.06 mole) are dissolved in three times its volume of acetone. The resulting solution is kept at 15° to 20° C, and a solution of 0.08 mole of triethylamine in three times its volume of acetone is gradually added dropwise to the solution with stirring. After the dropwise addition is completed, the solution is refluxed for 2 hours to complete the reaction and then cooled. The precipitated triethylamine hydrochloride is filtered off and the filtrate is distilled to remove acetone under reduced pressure. To the residual solution is added three times its volume of benzene and then the organic layer is treated by the same procedure as that described in the standard Method A to obtain the objective ester.

Method E: The reaction between an arylsulfonate of the alcohol of the formula (II) and a carboxylic acid salt of the formula (III)

An arylsulfonate (0.05 mole) is dissolved in three times its volume of acetone and 0.06 mole of a sodium carboxylate (which has been prepared by reacting equimolar amounts of the carboxylic acid and sodium hydroxide in water and distilling off water to obtain dry mass) is gradually added to the solution at room temperature with stirring. After the addition, the mixture is refluxed for 30 minutes to complete the reaction. After cooling, the deposited solid matter is filtered off and the filtrate is distilled to remove acetone under reduced pressure. The residue is dissolved in three times its volume of benzene and then the same after-treatment as that described in the standard Method A is carried out to obtain the objective compound.

The esters obtained according to the above-mentioned standard procedures are shown in the following Table together with the starting materials from which they were prepared, which is not however to be interpreted as limiting the compounds of the invention thereto. The symbols (C) and (F) in the elementary analysis column mean a calculated value and found value, respectively.

Table

| Example No. | Starting Alcohol or its derivative | Material Cyclopropane-carboxylic acid or its derivative | Reaction method | Compound No. | Cyclopropanecarboxylic acid ester obtained Name | Yield (%) | Refractive index($n_D^{25}$) | Elementary analysis (%) | C | H | N |
|---|---|---|---|---|---|---|---|---|---|---|---|
|  | 2,3-Di-methylmalei-midomethyl | 2,2-Dimethyl-3-(2,2-di-chlorovinyl)- |  |  | 2,3-Dimethyl-maleimido-methyl 2',2'- |  |  | (F) (C) | 52.38 52.04 | 4.71 4.95 | 4.29 4.05 |

Table-continued

| Example No. | Starting Alcohol or its derivative | Material Cyclopropane-carboxylic acid or its derivative | Reaction method | Compound No. | Cyclopropanecarboxylic acid ester obtained Name | Yield (%) | Refractive index($n_D^{25}$) | Elementary analysis (%) | C | H | N |
|---|---|---|---|---|---|---|---|---|---|---|---|
| 1 | alcohol | cyclopropane-carboxylic acid chloride | A | (1) | dimethyl-3'-(2,2-dichlorovinyl)-cyclopropane-carboxylate | 95 | 1.5261 | as $C_{15}H_{17}Cl_2NO_4$ | | | |
| 2 | 2,3-Dimethylmaleimidomethyl alcohol | 2,2-Dimethyl-3-(2-chlorovinyl)-cyclopropane-carboxylic acid chloride | A | (2) | 2,3-Dimethylmaleimidomethyl 2',2'-dimethyl-3'-(2-chlorovinyl)-cyclopropane-carboxylate | 92 | 1.5074 | (F) 57.51 / (C) 57.78 / as $C_{15}H_{18}ClNO_4$ | 57.51 / 57.78 | 5.99 / 5.82 | 4.52 / 4.49 |
| 3 | 2-Methyl-3-ethyl-maleimidomethyl alcohol | 2,2-Dimethyl-3-(2,2-dichlorovinyl)-cyclopropane-carboxylic acid | B | (3) | 2-Methyl-3-ethylmaleimidomethyl 2'2'-dimethyl-3'-(2,2-dichlorovinyl)-cyclopropane-carboxylate | 71 | 1.5278 | (F) 53.73 / (C) 53.35 / as $C_{16}H_{19}Cl_2NO_4$ | 53.73 / 53.35 | 5.08 / 5.32 | 4.01 / 3.89 |
| 4 | 2,3-Dimethylmaleimidomethyl tosylate | Sodium 2,2-dimethyl-3-(2-chloro-1-propenyl)-cyclopropane-carboxylate | E | (4) | 2,3-Dimethylmaleimidomethyl 2',2'-dimethyl-3'-(2-chloro-1-propenyl)-cyclopropane-carboxylate | 79 | 1.5162 | (F) 59.74 / (C) 59.82 / as $C_{16}H_{20}ClNO_4$ | 59.74 / 59.82 | 6.45 / 6.20 | 4.22 / 4.10 |
| 5 | 2,3-Diethylmaleimidomethyl alcohol | 2,2-Dimethyl-3-(2,2-difluorovinyl)-cyclopropane-carboxylic acid chloride | A | (5) | 2,3-Diethylmaleimidomethyl 2',2'-dimethyl-3'-(2,2-difluorovinyl)-cyclopropane-carboxylate | 90 | 1.5029 | (F) 59.74 / (C) 59.82 / as $C_{17}H_{21}F_2NO_4$ | 59.74 / 59.82 | 6.45 | 4.22 |
| 6 | 2,3-Dimethylmaleimidomethyl chloride | 2,2-Dimethyl-3-(2,2-dibromovinyl)-cyclopropane-carboxylic acid | D | (6) | 2,3-Dimethylmaleimidomethyl 2',2'-dimethyl-3'-(2,2-dibromovinyl)-cyclopropane-carboxylate | 89 | 1.5457 | (F) 41.62 / (C) 41.40 / as $C_{15}H_{17}Br_2NO_4$ | 41.62 / 41.40 | 4.07 / 3.94 | 3.44 / 3.22 |
| 7 | 2-Methyl-3-n-propyl-maleimidomethyl alcohol | 2,2-Dimethyl-3-(2,2-dichlorovinyl)-cyclopropane-carboxylic acid anhydride | C | (7) | 2-Methyl-3-n-propyl-maleimidomethyl 2',2'-dimethyl-3'-(2,2-dichlorovinyl)-cyclopropane-carboxylate | 86 | 1.5289 | (F) 54.31 / (C) 54.56 / as $C_{17}H_{21}Cl_2NO_4$ | 54.31 / 54.56 | 5.89 / 5.66 | 3.87 / 3.74 |
| 8 | 2-Methyl-3-(o,p-dimethyl-phenyl)-maleimidomethyl alcohol | 2,2-Dimethyl-3-(2,2-dichlorovinyl)-cyclopropane-carboxylic acid chloride | A | (8) | 2-Methyl-3-(o,p-dimethyl-phenyl)-maleimidomethyl 2',2'-dimethyl-3'-(2,2-dichlorovinyl)-cyclopropane-carboxylate | 89 | 1.5531 | (F) 60.41 / (C) 60.56 / as $C_{22}H_{23}Cl_2NO_4$ | 60.41 / 60.56 | 5.60 / 5.31 | 3.46 / 3.21 |
| 9 | 2-Methyl-3-isopropyl-maleimidomethyl alcohol | 2,2-Dimethyl-3-(2-chlorovinyl)-cyclopropane-carboxylic acid | B | (9) | 2-Methyl-3-isopropyl-maleimidomethyl 2',2'-dimethyl-3'-(2-chlorovinyl)-cyclopropane-carboxylate | 71 | 1.5093 | (F) 59.97 / (C) 60.09 / as $C_{17}H_{22}ClNO_4$ | 59.97 / 60.09 | 6.78 / 6.53 | 4.39 / 4.12 |
| 10 | 2-Ethyl-3-n-propyl-maleimidomethyl alcohol | 2,2-Dimethyl-3-(2,2-dichlorovinyl)-cyclopropane-carboxylic acid anhydride | C | (10) | 2-Ethyl-3-n-propylmaleimidomethyl 2',2'-dimethyl-3'-(2,2-dichlorovinyl)-cyclopropane-carboxylate | 84 | 1.5294 | (F) 55.37 / (C) 55.68 / as $C_{18}H_{23}Cl_2NO_4$ | 55.37 / 55.68 | 6.20 / 5.97 | 3.78 / 3.61 |
| 11 | 2-Methyl-3-ethylmaleimidomethyl alcohol | 2,2-Dimethyl-3-(2-bromovinyl)-cyclopropane-carboxylic | A | (11) | 2-Methyl-3-ethylmaleimidomethyl 2',2'-dimethyl-3'- | 87 | 1.5379 | (F) 51.77 / (C) 51.90 / as $C_{16}H_{20}BrNO_4$ | 51.77 / 51.90 | 5.64 / 5.44 | 3.99 / 3.78 |

Table-continued

| Example No. | Starting Alcohol or its derivative | Material Cyclopropane-carboxylic acid or its derivative | Reaction method | Compound No. | Cyclopropanecarboxylic acid ester obtained Name | Yield (%) | Refractive index($n_D^{25}$) | Elementary analysis | | C | H | N |
|---|---|---|---|---|---|---|---|---|---|---|---|---|
| | | acid chloride | | | (2-bromovinyl)-cyclopropane-carboxylate | | | | | | | |
| 12 | 2,2-Dimethylmaleimidomethyl alcohol | 2,2-Dimethyl-3-(2-bromo-2-chlorovinyl)-cyclopropane-carboxylic acid | B | (12) | 2,2-Dimethylmaleimidomethyl 2',2'-dimethyl-3'-(2-bromo-2-chlorovinyl)-cyclopropane-carboxylate | 73 | 1.5396 | (F) (C) as $C_{15}H_{17}BrClNO_4$ | | 45.96 46.12 | 4.47 4.39 | 3.54 3.59 |
| 13 | 2-Methyl-3-ethylmaleimidomethyl alcohol | 2,2-Dimethyl-3-(2-bromo-1-propenyl)-cyclopropane-carboxylic acid chloride | A | (13) | 2-Methyl-3-ethylmaleimidomethyl 2',2'-dimethyl-3'-(2-bromo-1-propenyl)-cyclopropane-carboxylate | 84 | 1.5432 | (F) (C) as $C_{17}H_{22}BrNO_4$ | | 53.25 53.13 | 5.81 5.77 | 3.71 3.65 |
| 14 | 2-Methylmaleimidomethyl tosylate | Sodium 2,2-dimethyl-3-(2,2-dichlorovinyl)-cyclopropane-carboxylate | E | (14) | 2-Methylmaleimidomethyl 2',2'-dimethyl-3'-(2,2-dichlorovinyl)-cyclopropane-carboxylate | 77 | 1.5247 | (F) (C) as $C_{14}H_{15}Cl_2NO_4$ | | 50.59 50.62 | 4.82 4.55 | 4.09 4.22 |
| 15 | Maleimidomethyl alcohol | 2,2-Dimethyl-3-(2,2-dibromovinyl)-cyclopropane-carboxylic acid anhydride | C | (15) | Maleimidomethyl 2',2'-dimethyl-3'-(2,2-dibromovinyl)-cyclopropane-carboxylate | 87 | 1.5388 | (F) (C) as $C_{13}H_{13}Br_2NO_4$ | | 38.55 38.36 | 3.49 3.22 | 3.48 3.44 |
| 16 | 2,3-Dimethylmaleimidomethyl alcohol | 2,2-Dimethyl-3-(2,2-difluorovinyl)-cyclopropane-carboxylic acid chloride | A | (16) | 2,3-Dimethylmaleimidomethyl 2',2'-dimethyl-3'-(2,2-difluorovinyl)-cyclopropane-carboxylate | 83 | 1.5004 | (F) (C) as $C_{15}H_{17}F_2NO_4$ | | 57.70 57.50 | 5.54 5.47 | 4.66 4.47 |
| 17 | 2-Methyl-3-phenylmaleimidomethyl alcohol | 2,2-Dimethyl-3-(2,2-dichlorovinyl)-cyclopropane-carboxylic acid | B | (17) | 2,-Methyl-3-phenylmaleimidomethyl 2',2'-dimethyl-3'-(2,2-dichlorovinyl)-cyclopropane-carboxylate | 68 | 1.5748 | (F) (C) as $C_{20}H_{19}Cl_2NO_4$ | | 58.77 58.84 | 4.82 4.69 | 3.50 3.43 |
| 18 | 2-Methyl-3-allylmaleimidomethyl alcohol | 2,2-Dimethyl-3-(2,2-dichlorovinyl)-cyclopropane-carboxylic acid chloride | A | (18) | 2-Methyl-3-allylmaleimidomethyl 2',2'-dimethyl-3'-(2,2-dichlorovinyl)-cyclopropane-carboxylate | 86 | 1.5318 | (F) (C) as $C_{17}H_{19}Cl_2NO_4$ | | 54.79 54.85 | 5.23 5.14 | 3.98 3.76 |
| 19 | 2-Methyl-3-propargylmaleimidomethyl alcohol | 2,2-Dimethyl-3-(2,2-dibromovinyl)-cyclopropane-carboxylic acid chloride | A | (19) | 2-Methyl-3-propargylmaleimidomethyl 2',2'-dimethyl-3'-(2,2-dimbromovinyl)-cyclopropane-carboxylate | 89 | 1.5345 | (F) (C) as $C_{17}H_{17}Br_2NO_4$ | | 44.71 44.47 | 3.90 3.73 | 2.94 3.05 |
| 20 | 2-Methyl-3-(p-methylphenyl)-maleimidomethyl tosylate | Sodium 2,2-dimethyl-3-(2,2-dichlorovinyl)-cyclopropane-carboxylate | E | (20) | 2-Methyl-3-(p-methylphenyl)-maleimidomethyl 2',2'-dimethyl-3'-(2,2-dichlorovinyl)-cyclopropane-carboxylate | 73 | 1.5729 | (F) (C) as $C_{21}H_{21}Cl_2NO_4$ | | 59.49 59.72 | 5.24 5.01 | 3.37 3.32 |
| 21 | 2-Methyl-3-benzylmaleimidomethyl alcohol | 2,2-Dimethyl-3-(2,2-dichlorovinyl)-cyclopropane-carboxylic acid | C | (21) | 2-Methyl-3-benzylmaleimidomethyl 2',2'-dimethyl-3'-(2,2-di- | 81 | 1.5676 | (F) (C) as $C_{21}H_{21}Cl_2NO_4$ | | 59.84 59.72 | 5.11 5.01 | 3.19 3.32 |

Table-continued

| Example No. | Starting Alcohol or its derivative | Material Cyclopropane-carboxylic acid or its derivative | Reaction method | Compound No. | Cyclopropanecarboxylic acid ester obtained Name | Yield (%) | Refractive index($n_D^{25}$) | Elementary analysis | (%) C | H | N |
|---|---|---|---|---|---|---|---|---|---|---|---|
| 22 | 2-Allyl-maleimido-methyl alcohol | 2,2-Dimethyl-3-(2-chloro-1-propenyl)-cyclopropane-carboxylic acid chloride | A | (22) | 2-Allyl-maleimido-methyl 2',2'-dimethyl-3'-(2-chloro-1-propenyl)-cyclopropane-carboxylate | 84 | 1.5364 | (F)<br>(C)<br>as $C_{17}H_{20}ClNO_4$ | 60.18<br>60.44 | 6.04<br>5.97 | 4.33<br>4.15 |
| 23 | 2-Methyl-3-(m-methyl-phenyl)-maleimido-methyl chloride | 2,2-Dimethyl-3-(2,2-di-chlorovinyl)-cyclopropane carboxylic acid | D | (23) | 2-Methyl-3-(m-methyl-phenyl)-maleimido-methyl 2',2'-dimethyl-3'-(2,2-di-chlorovinyl)-cyclopropane-carboxylate | 74 | 1.5712 | (F)<br>(C)<br>as $C_{21}H_{21}Cl_2NO_4$ | 59.90<br>59.72 | 5.07<br>5.01 | 3.46<br>3.32 |
| 24 | 2-Methyl-3-(p-chloro-phenyl)-maleimido-methyl alcohol | 2,2-Dimethyl-3-(2-bromo-1-propenyl)-cyclopropane-carboxylic acid | B | (24) | 2-Methyl-3-(p-chloro-phenyl)-maleimido-methyl 2',2'-dimethyl-3'-(2-bromo-1-propenyl)-cyclopropane-carboxylate | 79 | 1.5783 | (F)<br>(C)<br>as $C_{21}H_{21}BrClNO_4$ | 54.25<br>54.04 | 4.66<br>4.53 | 2.87<br>3.00 |
| 25 | 2-Methyl-3-(p-ethyl-phenyl)-maleimido-methyl alcohol | 2,2-Dimethyl-3-(2-chloro-vinyl)-cyclopropane-carboxylic acid chloride | A | (25) | 2-Methyl-3-(p-ethyl-phenyl)-maleimido-methyl 2',2'-dimethyl-3'-(2-chloro-vinyl)-cyclopropane-carboxylate | 92 | 1.5567 | (F)<br>(C)<br>as $C_{22}H_{24}ClNO_4$ | 65.73<br>65.75 | 6.31<br>6.02 | 3.53<br>3.49 |
| 26 | 2-Methyl-3-(m-methyl-phenyl)-maleimido-methyl alcohol | 2,2-Dimethyl-3-(2,2-di-fluorovinyl)-cyclopropane-carboxylic acid chloride | A | (26) | 2-Methyl-3-(m-methyl-phenyl)-maleimido-methyl 2',2'-dimethyl-3'-(2,2-di-fluorovinyl)-cyclopropane-carboxylate | 95 | 1.5474 | (F)<br>(C)<br>as $C_{21}H_{21}F_2NO_4$ | 64.94<br>64.77 | 5.62<br>5.44 | 3.78<br>3.60 |
| 27 | 2-Methyl-3-(1-pro-penyl)-maleimido-methyl alcohol | 2,2-Dimethyl-3-(2,2-di-bromovinyl)-cyclopropane-carboxylic acid chloride | A | (27) | 2-Methyl-3-(1-propenyl)-maleimido-methyl 2',2'-dimethyl-3'-(2,2-di-bromovinyl)-cyclopropane-carboxylate | 88 | 1.5499 | (F)<br>(C)<br>as $C_{17}H_{19}Br_2NO_4$ | 44.06<br>44.27 | 4.27<br>4.15 | 3.21<br>3.04 |
| 28 | 2-Phenyl-maleimido-methyl alcohol | 2,2-Dimethyl-3-(2,2-di-chlorovinyl)-cyclopropane-carboxylic acid anhydride | C | (28) | 2-Phenyl-maleimido-methyl 2',2'-dimethyl-3'-(2,2-di-chlorovinyl)-cyclopropane-carboxylate | 86 | 1.5727 | (F)<br>(C)<br>as $C_{19}H_{17}Cl_2NO_4$ | 58.02<br>57.88 | 4.30<br>4.35 | 3.65<br>3.55 |
| 29 | 2-Methyl-3-(m-chloro-phenyl)-maleimido-methyl alcohol | 2,2-Dimethyl 3-(2-chloro-vinyl)-cyclopropane-carboxylic acid chloride | A | (29) | 2-Methyl-3-(m-chloro-phenyl)-maleimido-methyl 2',2'-dimethyl-3'-(2-chloro-vinyl)-cyclopropane-carboxylate | 93 | 1.5706 | (F)<br>(C)<br>as $C_{20}H_{19}Cl_2NO_4$ | 58.69<br>58.84 | 4.80<br>4.69 | 3.59<br>3.43 |

In order to demonstrate the excellent effects of the present compounds more clearly, the experimental examples and their results will be shown below.

EXPERIMENTAL EXAMPLE 1

Each of the present compounds (1) to (29) and pyrethrin was respectively formulated into each of a 0.1% oil spray using deodorized kerosene.

Twenty Northern house mosquito adults (*Culex pipiens pallens*) per group or 20 house-fly adults (*Musca domestica*) per group were liberated in a (70 cm)³ glass chamber. Each of 0.7 ml of oil sprays obtained was sprayed under the pressure of 20 lb/inch² and a knock-down ratio after 5 minutes was obtained. The result is shown in Table 1.

Table 1

| Test Compound (0.1 % oil spray) | | Knock-down ratio (%) after 5 minutes | |
|---|---|---|---|
| | | Northern house mosquito adults | House-fly adults |
| Present compound | (1) | 100 | 100 |
| " | (2) | 100 | 100 |
| " | (3) | 100 | 100 |
| " | (4) | 100 | 100 |
| " | (5) | 100 | 95 |
| " | (6) | 100 | 100 |
| " | (7) | 95 | 90 |
| " | (8) | 80 | 80 |
| Present compound | (9) | 90 | 90 |
| " | (10) | 100 | 95 |
| " | (11) | 95 | 95 |
| " | (812) | 100 | 100 |
| " | (13) | 90 | 90 |
| " | (14) | 80 | 75 |
| " | (15) | 75 | 80 |
| " | (16) | 100 | 100 |
| " | (17) | 80 | 75 |
| " | (18) | 90 | 90 |
| " | (19) | 100 | 100 |
| " | (20) | 80 | 80 |
| " | (21) | 75 | 70 |

Table 1-continued

| Test Compound (0.1 % oil spray) | | Knock-down ratio (%) after 5 minutes | |
|---|---|---|---|
| | | Northern house mosquito adults | House-fly adults |
| " | (22) | 75 | 70 |
| " | (23) | 80 | 75 |
| " | (24) | 85 | 85 |
| " | (25) | 70 | 70 |
| " | (26) | 90 | 95 |
| " | (27) | 80 | 75 |
| " | (28) | 70 | 70 |
| " | (29) | 75 | 70 |
| Pyrethrin (control) | | 60 | 45 |

EXPERIMENTAL EXAMPLE 2

Each of the present compounds (1), (2), (3), (6), (12), (19) and (28), the dl-trans acid isomer of the compounds (4), (16) and (23), and the following control compounds was respectively formulated into a 0.3% mosquito coil.

Twenty Northern house mosquito adults (*Culex pipiens pallens*) per group or 20 house-fly adults (*Musca domestica*) per group were liberated in a (70 cm)³ glass chamber. Each of one gram of the mosquito coils obtained was ignited at the both ends and placed at the center of the chamber. The number of knocked down insects with lapse of time was counted. This test was repeated several times and the value of $KT_{50}$ (Time required for 50% knock-down) was obtained from the test results. The result is shown in Table 2.

Table 2

| Test Compound (0.3 % mosquito coil) | $KT_{50}$ (min. sec.) | |
|---|---|---|
| | Northern house mosquito adults | house-fly adults |
| Present compound (1) | 9'30" | 12'15" |
| Present compound (2) | 11'07" | 16'21" |
| Present compound (3) | 10'05" | 13'00" |
| dl-trans acid isomer of Present compound (4) | 12'36" | 18'25" |
| Present compound (6) | 10'10" | 13'14" |
| Present compound (12) | 10'40" | 13'22" |
| dl-trans acid isomer of Present compound (16) | 11'06" | 16'40" |
| Present compound (19) | 12'13" | 13'57" |
| dl-trans acid isomer of Present compound (23) | 13'00" | 19'18" |
| Present compound (28) | 12'39" | 18'33" |
| Control (allethrin)** | 14'00" | >24' |

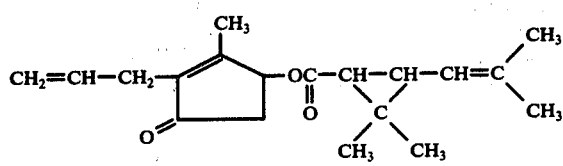

Control*  13'20"  22'00"

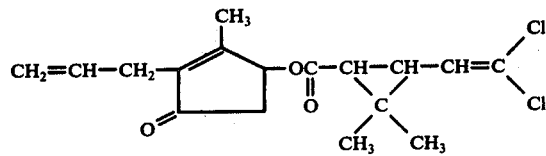

Control (tetramethrin)**  15'12"  21'06"

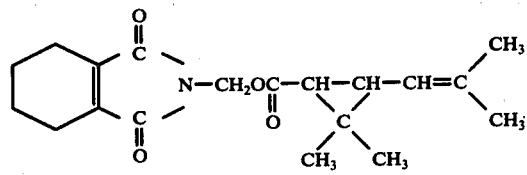

Control*  14'18"  20'09"

Table 2-continued

| Test Compound (0.3 % mosquito coil) | KT$_{50}$ (min. sec.) Northern house mosquito adults | house-fly adults |
|---|---|---|
| [structure: phthalimide-N-CH$_2$OC(=O)-CH-CH-CH=CCl$_2$ with C(CH$_3$)$_2$ cyclopropane] | | |
| Control* | 17'05" | 21'33" |
| [structure: benzyl-furfuryl ester with dichlorovinyl cyclopropane] | | |
| Control* | 18'30" | >24' |
| [structure: phenoxybenzyl ester with dichlorovinyl cyclopropane] | | |

Note:
*Compounds described in Japanese Laid-Open No. 47531/1974
**Commercially available compounds

EXPERIMENTAL EXAMPLE 3

Each of the present compounds (1), (2), (4), (6), (11), (12), (13), (16), (19), (23), (26) and (28), the d-trans acid isomer of the compound (1) and the following control compounds was respectively formulated into a 0.1 % oil spray using deodorized kerosene.

The value of KT$_{50}$ (Time required for 50 % knockdown) of each oil spray on Northern house mosquito was obtained in the same manner as described in Experimental Example 1. Further the knocked down insects were collected and transferred into an another chamber, and then the mortality after 24 hours was checked. The result is shown in Table 3.

Table 3

| Test Compound (0.1% oil spray) | Northern house mosquito KT$_{50}$ (sec.) | Mortality after 24 hours (%) |
|---|---|---|
| Present compound (1) | 53" | 100 |
| Present compound (2) | 70" | 100 |
| Present compound (4) | 75" | 100 |
| Present compound (6) | 74" | 100 |
| Present compound (11) | 78" | 100 |
| Present compound (12) | 67" | 100 |
| Present compound (13) | 82" | 100 |
| Present compound (16) | 72" | 100 |
| Present compound (19) | 79" | 100 |
| Present compound (23) | 105" | 100 |
| Present compound (26) | 103" | 95.0 |
| Present compound (28) | 126" | 95.0 |
| d-trans acid isomer of Present compound (1) | 30" | 100 |
| Control (allethrin)*** | 324" | 65.0 |
| Control* [structure with dichlorovinyl] | 295" | 80.0 |
| Control (tetramethrin)*** | 135" | 80.0 |

Table 3-continued

| Test Compound (0.1% oil spray) | Northern house mosquito | |
|---|---|---|
| | KT$_{50}$ (sec.) | Mortality after 24 hours (%) |
| Control* [structure: hexahydrophthalimide-N-CH₂OC(O)-CH-CH-CH=C(CH₃)₂ with gem-dimethyl cyclopropane] | 130" | 84.2 |
| Control* [structure: hexahydrophthalimide-N-CH₂OC(O)-CH-CH-CH=CCl₂ with gem-dimethyl cyclopropane] | 256" | 94.7 |
| Control* [structure: benzyl-furfuryl-CH₂OC(O)-CH-CH-CH=CCl₂ with gem-dimethyl cyclopropane] | 328" | 93.3 |
| Control* [structure: phenoxybenzyl-CH₂OC(O)-CH-CH-CH=CCl₂ with gem-dimethyl cyclopropane] | 145" | 90.0 |
| Control** [structure: CH≡C-CH₂-furyl-CH₂OC(O)-CH-CH-CH=CCl₂ with gem-dimethyl cyclopropane] | 141" | 77.8 |
| Control (pyrethrin)*** [structure: dimethylmaleimide-N-CH₂OC(O)-CH-CH-CH=C(CH₃)₂ with gem-dimethyl cyclopropane] | 150" | 89.5 |

Note:
*Compounds described in Japanese Laid-Open No. 47531/1974
**Compounds described in French Patent No. 1434956
***Commercially available compounds

EXPERIMENTAL EXAMPLE 4

Each of the present compounds (1), (2), (3), (5), (7), (8), (10), (12), (14), (18), (24) and (27), and the following control compounds was respectively formulated into a 0.025% oil spray using deodorized kerosene.

Ten cockroaches were released into a plastic cup (having 9.5 cm of diameter and 4 cm of height) and covered with a 16-mesh nylon net, and then the cup was placed on bottom of a glass cylinder having 10 cm of diameter and 37 cm of height. 0.5 Milliliter of an oil spray formulation was sprayed into the glass cylinder through an atomizer at a pressure of 0.6 kg/cm². Then, the glass cylinder was immediately covered with a glass lid. The number of knocked down insects with the lapse of time was observed. This test was repeated several times and the value of KT$_{50}$ (Time required for 50% knock-down) was obtained from the test results. The result is shown in Table 4.

Table 4

| Test Compound (0.025 % oil spray) | German cockroach KT$_{50}$ (min. sec.) |
|---|---|
| Present Compound (1) | 3'30" |
| Present Compound (2) | 4'40" |
| Present Compound (3) | 4'00" |
| Present Compound (5) | 5'10" |
| present Compound (7) | 6'30" |
| Present Compound (8) | 7'20" |
| Present Compound (10) | 5'00" |
| Present Compound (12) | 4'20" |
| Present Compound (14) | 7'50" |

Table 4-continued

| Test Compound (0.025 % oil spray) | German cockroach KT$_{50}$ (min. sec.) |
|---|---|
| Present Compound (18) | 6'40" |
| Present Compound (24) | 7'00" |
| Present Compound (27) | 8'00" |
| Control (allethrin)*** | >20' |
| Control* (structure: allyl-methyl-cyclopentenone ester with dimethyl-isobutenyl-cyclopropane) | 20'00" |
| Control (tetramethrin)*** (structure: allyl-methyl-cyclopentenone ester with dichlorovinyl-dimethyl-cyclopropane) | 13'10" |
| Control* (tetrahydrophthalimide N-CH$_2$O ester with dimethyl-isobutenyl-cyclopropane) | 10'20" |
| Control* (tetrahydrophthalimide N-CH$_2$O ester with dichlorovinyl-dimethyl-cyclopropane) | >20' |
| Control* (benzylfuryl-CH$_2$O ester with dichlorovinyl-dimethyl-cyclopropane) | >20' |
| Control* (phenoxyphenyl-CH$_2$O ester with dichlorovinyl-dimethyl-cyclopropane) | 17'40" |
| Control** (propargyl-furyl-CH$_2$O ester with dichlorovinyl-dimethyl-cyclopropane) | 15'20" |
| Control (pyrethrin)*** (dimethylmaleimide N-CH$_2$O ester with dimethyl-isobutenyl-cyclopropane) | 10'30" |

Note:
*Compounds described in Japanese Laid-Open No. 47531/1974
**Compoundsdescribed in French Pat. No. 1434956
***Commercially available compounds These experiments mean that the present compounds are superior to the control compounds such as allethrin, pyrethrin and the like. Further, owing to the above-mentioned features, the present insecticides and acaricides can widely be used for knocking down or killing insects harmful to public health, for example, houseflies, mosquitoes and cockroaches, and insects harmful in stored cereals, for example, grain mite, indian meal moth and rice weevils. Moreover, the present pesticides are extremely effective for knocking down and killing insects harmful in agriculture, horticulture and forestry, for example, planthoppers, leafhoppers, army worms and cut worms, diamond-back moth, tortorixes, aphids, stem-borers, mites and Japanese giant silk moth; and animal-parasitic lice and mites. The present pesticides can also be used for controlling a wide range of other harmful insects.

The insecticides and acaricides of the present invention not only cause the harmful insects to be knocked down and to die, byt also they have repellency (the effect of keeping harmful insects away from their host plant). In particular, they are also very superior in that they can freely be used, due to their low toxicity and harmlessness in mammals, for agricultural crops before harvest, household horticulture, green-house cultivation and food-packaging.

In the practical application of the present compounds, they be applied alone or in combination with a carrier for the convenience of use as a pesticide. The present compounds can be formulated into optional preparation forms without any special treating conditions according to the formulation of common pesticides. That is, the compounds are formulated into emulsifiable concentrate, wettable powder, dust, granules, fine granules, oil spray, aerosol, heating fumigant (mosquito coil, electric mosquito killer), thermal fogging agent, non-heating fumigant and bait by the methods well known to the skilled in the art, and they are used in the form and in the combination with a carrier which are suitable for the application method.

Furthermore, the insecticidal activity of the present compounds can be increased in combination with known synergists for pyrethroid such as α-[2-(2-butoxyethoxy)-ethoxy]-4,5-methylenedioxy-2-propyltoluene (hereinafter referred to as piperonylbutoxide), 1,2-methylenedioxy-4-[2-(octylsulfinyl)-propyl]-benzene (hereinafter referred to as sulfoxide), 4-(3,4-methylenedioxyphenyl)-5-methyl-1,3-dioxane (hereinafter referred to as sulfoxane), N-(2-ethylhexyl)-bicyclo[2,2,1]hepta-5-ene-2,3-dicarboximide (hereinafter referred to as MGK-264), octachlorodipropyl ester (hereinafter referred as S-421), and isobornylthiocyano acetate (hereinafter referred to as Thanite); and with known synergists for allethrin or pyrethrin.

In general, the chrysanthemate type compounds tend to be inferior in the resistance to light, heat and oxidation. Accordingly, compositions having a more stable activity can be prepared by adding a proper amount of stabilizing agents, for example, antioxidants or U.V. absorbers such as phenol derivatives including BHT and BHA, bisphenol derivatives, arylamine derivatives including phenyl-α-naphthylamine, phenyl-β-naphthylamine and condensation products of phenetidine and acetone, and benzophenone compounds.

Additionally, the present compounds can be formulated into multipurpose compositions having more superior activity in combination with other active ingredients such as allethrin, N-(chrysanthemoxymethyl)-3,4,5,6-tetrahydrophthalimide (hereinafter referred to as tetramethrin), 5-benzyl-3-furylmethyl chrysanthemate (hereinafter referred to as resmethrin), 3-phenoxybenzyl chrysanthemate, 5-propargylfurfuryl chrysanthemate and 2-methyl-5-propargyl-3-furylmethyl chrysanthemate; isomers thereof, for example, d-trans-, and d-cis,trans-chrysanthemic acid esters thereof; pyrethrum extracts; d-trans-, or d-cis,trans-chrysanthemic acid esters of a d-allethrolone; other well-known cyclopropanecarboxylic acid esters; organochlorine type insecticides, for example DDT, BHC and methoxychlor; organophosphorus type insecticides, for example, 0,0-dimethyl-0-(3-methyl-4-nitrophenyl)-phosphorothioate (hereinafter referred to as Sumithion (a registered trademark of Sumitomo Chemical Company, Limited)), 0,0-dimethyl-0-4-cyanophenyl-phosphorothioate (hereinafter referred to as Cyanox (a registered trademark of Sumitomo Chemical Company, Limited)) and 0,0-dimethyl-0-(2,2-dichlorovinyl)-phosphate (hereinafter referred to as DDVP); carbamate type insecticides, for example, 1-naphthyl-N-methylcarbamate and 3,5-dimethylphenyl-N-methylcarbamate (hereinafter referred to as Meobal (a registered trademark of Sumitomo Chemical Company Limited)); other insecticides, fungicides, nematocides, acaricides, herbicides, plant growth regulators, fertilizers, microbial insecticides e.g. B.t. and B.m.; insect hormone compounds; or other agricultural chemicals. Furthermore a synergistic effect due to the combination can also be expected.

Preparation of the present insecticides and acaricides, and lethal effect thereof will be illustrated with reference to the following preparation examples and application examples.

PREPARATION EXAMPLE 1

Each of 0.2 part of the present compounds (1), (2), (6), (12) and (19) is respectively dissolved in kerosene to make the total weight 100 parts. Thus each oil spray is obtained.

PREPARATION EXAMPLE 2

Each of 0.5 part of the present compounds (1), (2), (4), (6), (10), (11), (12), (16) and (23) is dissolved in kerosene to make the total weight 100 parts. Thus each oil spray is obtained. In the same manner, each of 0.5 part of dl-trans acid isomer of the present compounds (3), (8), (13), (17) and (26) is formulated into an oil spray.

PREPARATION EXAMPLE 3

To each of 0.1 part of the present compounds (1), (2), (6) and (12), 0.5 part of piperonybutoxide is added and each is dissolved in kerosene to make the total weight 100 parts. Thus, each oil spray is obtained. In the same manner 0.1 part of the dl-trans acid isomer of the present compound (19) is formulated into an oil spray.

PREPARATION EXAMPLE 4

To each of 10 parts of the present compounds (1) to (29) are added 20 parts of S-421, 15 parts of Sorpol SM-200 (a registered trade mark of Toho Kagaku Co., Ltd.) and 55 parts of xylene. Then each mixture is thoroughly mixed to make a solution. Thus each emulsifiable concentrate is obtained.

PREPARATION EXAMPLE 5

To each of 20 parts of the present compounds (1), (4), (12), (16), (23) and (27) are added 15 parts of Sorpol SM-200 (the same as above) and 65 parts of xylene. Then each mixture is thoroughly mixed to make a solution. Thus each emulsifiable concentrate is obtained. In the same manner, each of 20 parts of dl-trans acid isomer of the present compounds (6), (18) and (26) is formulated into an emulsifiable concentrate.

PREPARATION EXAMPLE 6

To each of 0.1 part of the present compounds (1), (6) and (12) are respectively added and mixed 0.2 part of resmethrin, 7 parts of xylene and 7.7 parts of deodorized kerosene to make each solution. Then each solution is filled into an aerosol container. After attaching a valve portion to the container, 85 parts of a propellant (e.g. liquefied petroleum gas) is charged therein under pressure through the valve. Each aerosol is thus obtained.

PREPARATION EXAMPLE 7

To each of 0.3 part of the present compounds (2) and (16) are respectively added and mixed 0.1 part of the d-trans acid isomer of resmethrin, 7 parts of xylene and 7.6 parts of deodorized kerosene to make each solution. Then each solution is filled into an aerosol container. After attaching a valve portion to the container, 85 parts of a propellant (e.g. liquefied petroleum gas) is charged therein under pressure through the valve. Each aerosol is thus obtained. In the same manner, 0.3 part of the dl-trans acid isomer of the compound (23) is formulated into an aerosol.

PREPARATION EXAMPLE 8

0.1 Part of the present compound (1), 0.2 part of the d-trans acid isomer of resmethrin, 11.7 parts of deodorized kerosene and 1 part of Atmos 300 (a registered trademark of Atlas Chemical Co.) are thoroughly mixed and emulsified by the addition of 50 parts of pure water. An aerosol container is then filled with the resulting emulsion and 35 parts of a 3 : 1 mixture of deodorized butane to deodorized propane. A water-based aerosol is thus obtained.

PREPARATION EXAMPLE 9

To each of 0.2 part of each d-trans acid isomer of the present compounds (4), (6), (12), (16), (19) and (27) are respectively added and mixed 0.1 part or resmethrin, 7 parts of xylene and 7.7 parts of deodorized kerosene to make each solution. Then each solution is filled into an aerosol container. After attaching a valve portion to the container, 85 parts of a propellant (e.g. liquefied petroleum gas) is charged therein under pressure through the valve. Each aerosol is thus obtained.

PREPARATION EXAMPLE 10

To each of 0.3 g of each d-trans acid isomer of the present compounds (2), (5), (14), (22) and (26) are respectively added 0.3 g of allethrin and 0.6 g of BHT and each mixture is respectively dissolved in 20 ml of methanol. Then each solution is uniformly mixed with 98.8 g of a mosquito coil carrier containing Tabu powder, Pyrethrum marc and wood powder in a ratio of 3 : 5 : 1, and then methanol is evaporated. To each residue obtained is added 150 ml of water and the mixture is kneaded thoroughly, shaped into a mosquito coil and dried. Thus, each mosquito coil is obtained.

PREPARATION EXAMPLE 11

Each of 0.5 g of the present compounds (1), (6) and (19) is respectively dissolved in 20 ml of methanol. The solution is uniformly mixed with 99.5 g of a mosquito coil carrier (the same as above) and then methanol is evaporated. To each residue obtained is added 150 ml of water and the mixture is kneaded thoroughly, shaped into a mosquito coil and dried. Thus, each mosquito coil is obtained.

PREPARATION EXAMPLE 12

0.1 Gram of the dl-trans acid isomer of the present compounds (6), 0.1 g of BHT and 0.1 g of piperonylbutoxide are dissolved in a suitable amount of chloroform. The solution is impregnated uniformly in a filter paper having 3.5 cm × 1.5 cm of area and 0.3 cm of thickness.

Thus a fibrous fumigant for heating on a hot plate is obtained. Materials having an effect equivalent to pulp plate such as filter paper, for example, asbestos may also be used as a fibrous carrier.

PREPARATION EXAMPLE 13

0.02 Gram of the present compound (1), 0.05 g of 5-propargylfurfuryl dl-cis,trans-chrysanthemate and 0.1 g of BHT are dissolved in a suitable amount of chloroform. The solution is absorbed uniformly in a filter paper having 3.5 cm × 1.5 cm of area and 0.3 cm of thickness.

Thus, a fibrous fumigant for heating on a hot plate is obtained.

PREPARATION EXAMPLE 14

Each of 20 parts of the present compounds (3), (6), (12), (20) and (29) is respectively mixed thoroughly with 10 parts of Sumithion (the same as above) and 5 parts of Sorpol SM-200 (the same as above). Then each mixture is respectively mixed with 65 parts of 300 mesh talc in a mortar while thoroughly stirring. Thus, each wettable powder is obtained. In the same manner, each of 20 parts of each dl-trans acid isomer of the present compounds (10), (16) and (24) is formulated into an wettable powder.

PREPARATION EXAMPLE 15

To each of 1 part of the present compounds (1), (2), (6), (8), (10), (16), (18), (23) and (25) is respectively added 2 parts of 1-naphthyl-N-methyl-carbamate and the mixture is dissolved in 20 parts of acetone, and then 97 parts of 300 mesh diatomaceous earth is added thereto. After thoroughly mixing in a mortar while stirring, acetone is removed by evaporation. Thus each dust is obtained.

PREPARATION EXAMPLE 16

Each of 3 parts of the present compounds (1), (6), (10), (12), (16), (20) and (26) is thoroughly mixed in a mortar together with 5 parts of Toyolignin CT (a registered trademark of Toyo Spinning Co., Ltd.) and 92 parts of GSM Clay (a registered trademark of Zieklite Mining Co., Ltd.).

Then each mixture is respectively mixed with water in a 10% amount based on the weight of the mixture, granulated by means of a granulator and airdried. Thus each granular preparation is obtained. In the same manner, 3 parts each of each dl-trans acid isomer of the present compounds (7) and (19) is formulated into a granular preparation.

PREPARATION EXAMPLE 17

Each of 4 parts of the present compounds (1), (4), (9), (15), (17), (21), (24) and (28) is respectively thoroughly mixed in a mortar together with 2 parts of Cyanox (the same as above), 5 parts of Toyolignin CT (a registered trademark of Toyo Spinning Co., Ltd.) and 89 parts of GSM Clay (a registered trademark of Zieklite Mining Co., Ltd.).

Then each mixture is mixed with 10% by weight of water based on the weight of the mixture, granulated by means of a granulator and air-dried. Thus, each fine granular preparation is obtained.

The insecticidal and acaricidal activities of the present compositions thus obtained are as follows.

APPLICATION EXAMPLE 1

Each of 5 ml of the oil sprays formulated by the Preparation Examples 1, 2, and 3 was sprayed, according to the Campbel's turn table method [Soap and Sanitary Chemicals, Vol. 14, No. 6, 119 (1938)]. About 100 house-fly adults (*Musca domestica*) per group were exposed to the descending mist for 10 minutes. By the next day, more than 80% of the flies were killed in each case.

APPLICATION EXAMPLE 2

Each of the emulsifiable concentrates formulated according to the Preparation Example 4 was respectively diluted 10,000 times with water. Two liters each of each test emulsion so prepared was taken in a polystyrene case having 23 cm × 30 cm of area and 6 cm of depth, and about 100 full grown larvae of Northern house mosquito (*Culex pipiens pallens*) were liberated therein. By the next day, more than 90% of the larvae were killed in each case.

APPLICATION EXAMPLE 3

In a 1/50,000 Wagner's pot, rice plants which had elapsed 45 days after sowing were grown. Each of the emulsifiable concentrates formulated according to the Preparation Example 4 was respectively diluted 200 a times with water. Each test solution so prepared was individually sprayed on the rice plants in an amount ratio of 10 ml per pot. Each pot was covered with wire net and about 30 adults of green rice leafhoppers (Nephotettix cincticeps) were liberated in the pot. After one day, more than 90% of the leafhoppers were killed in each case.

APPLICATION EXAMPLE 4

Each of the emulsifiable concentrates formulated according to the Preparation Example 4 was diluted 200 times with water. About 10 larvae of tabacco cut worm (*Spodoptera litura*) in the third to fourth instar stage were liberated in a glass Petri dish having 14 cm of inside diameter and 1 ml each of dilute solutions was sprayed. Thereafter, the larvae were liberated in another dish in which feed had previously been placed. After two days, more than 90% of the larvae were killed in each case.

APPLICATION EXAMPLE 5

The insecticidal activity on house-fly adults (*Musca domestica*) of each aerosol formulated according to the Preparation Examples 6, 7, 8 and 9 was tested by the aerosol test method (Soap and Chemical Specialities, Blue Book, 1965) using a (6 ft)³ Peet Grady's chamber. Thus, with each aerosol, more than 80% of the flies were knocked down 15 minutes after spraying and more than 70% of the flies were killed by the next day.

APPLICATION EXAMPLE 6

About 50 Northern house mosquito adults (*Culex pipiens pallens*) were liberated in a (70 cm)³ glass chamber in which a battery-type small electric fan (having wind diameter of 13 cm) was located and driven. Each of 0.1 g of each mosquito coil formulated according to the Preparation Examples 10 and 11 was ignited at one end and placed at the center of the bottom of the chamber. With each mosquito coil, more than 90% of the adults were knocked down within 20 minutes and more than 80% of the adults were killed by the next day.

APPLICATION EXAMPLE 7

About 50 house-fly adults (*Musca domestica*) were liberated in a (70 cm)³ glass chamber in which a battery-type small electric fan (having wing diameter of 13 cm) was located and driven. Each of the fumigants formulated according to the Preparation Examples 12 and 13 was placed on a hot plate in the chamber and fumigated. More than 90% of the house-flies were knocked down within 20 minutes with each fumigant.

APPLICATION EXAMPLE 8

About 20 rice plants were grown up to a 3 to 4-leaf stage in a flower pot having 10 cm of diameter, and then a 200-fold aqueous dilute solution of each wettable powder formulated according to the Preparation Example 14 was applied thereto by means of a turn table. After air-drying, each pot was covered with a wire cage and 20 to 30 smaller brown planthopper adults (*Laodelphax striatellus*) were liberated therein. The dead and alive after 24 hours were counted and more than 80% of the mortality was obtained in each case.

APPLICATION EXAMPLE 9

A glass Petri dish having 14 cm of diameter was coated on the inside wall with butter, leaving at the lower part an uncoated portion of 1 cm in width. Onto the bottom of the dish, each of the dusts formulated according to the Preparation Example 15 was uniformly dusted in a proportion of 2 g/m².

Subsequently, 10 German cockroach adults (*Blattela germanica*) per group were liberated in the dish and contacted with the dust for 30 minutes. After three days, more than 90% of the knocked down cockroaches were killed in each case.

APPLICATION EXAMPLE 10

Ten liters of water were introduced into a 14 liter polypropylene bucket, and 1 g of the granular preparations formulated according to the Preparation Examples 16 and 17 was added thereto. After one day, about 100 full grown Northern house mosquito larvae (*Culex pipiens pallens*) were liberated in the water. The dead and alive were counted and more than 90% of the larvae were killed within 24 hours in each case.

APPLICATION EXAMPLE 11

Rice plants were grown up to the tilling stage in a 1/100,000 Wagner's pot and the water depth was kept at 5 cm. Each of the granular preparations formulated according to the Preparation Example 16 was applied thereto in a ratio of 10 kg/10 ares. Thereafter, each pot was covered with a wire cage and smaller brown planthopper adults (*Laodelphax striatellus*) were liberated therein. After 24 hours, more than 90% of the adults were killed in each case.

APPLICATION EXAMPLE 12

Three grams each of the oil sprays formulated according to the Preparation Example 1 was fogged, by means of an insect fogger (Burgess Vibrocrafters INC., America), into a Peet Grady's chamber (the same as in Example 5) in which about 500 house-fly adults (*Musca domestica*) had previously been liberated. After 30 minutes, more than 90% of the adults were knocked down in each case.

APPLICATION EXAMPLE 13

Carmine mite female adults (*Tetranychus cinnabarinus*) were made parasitic on leaves of the potted kidney bean 82-leaf stage) which had elapsed 9 days after sowing, in a proportion of 10-15/leaf, and bred at 27° C for a week in a constant temperature room. Then, numerous carmine mites were found to be bred at various growth stages. At this time a 200-fold aqueous dilute solution of each emulsifiable concentrate formulated according to the Preparation Example 5 was sprayed in a ratio of 10 ml/pot by means of a turn table. After 10 days, damage of kidney bean by the mites was observed.

As the result, an increase of the damage was not observed in any case.

APPLICATION EXAMPLE 14

Tea branches were put into water in a Erlenmeyer flask and a 200-fold aqueous dilute solution of each emulsifiable concentrate formulated according to the Preparation Example 5 was sprayed in a ratio of 10 ml/branch by means of a turn table. Then larvae of tea leaf roller (*Caloptilia theivora*) were made parasitic in a ratio of 10 larvae/branch and after 3 days, the number of rolled leaves were counted.

As the result, rolled leaves were not found in any case.

APPLICATION EXAMPLE 15

Engorged female adults of bull tick (*Boophilus microplus*) belonging to the animal-parasitic mites were dipped in a 400-fold aqueous dilute solution of each emulsifiable concentrate formulated according to the Preparation Example 5 and then oviposition of the dipped adults was observed.

As a result, the suppression percentage of oviposition of the treated adults was more than 80% in each case when the suppression percentage of oviposition of untreated adults was taken as 0%.

What is claimed is:

1. A cyclopropanecarboxylic acid ester of the formula (I),

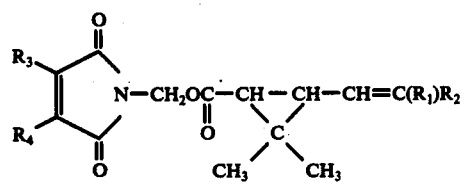

wherein $R_1$ is a hydrogen atom, methyl group or a fluorine, chlorine or bromine atom, $R_2$ is a fluorine, chlorine or bromine atom, and each of $R_3$ and $R_4$ is independently a hydrogen atom, a $C_1$-$C_3$ alkyl, $C_2$-$C_3$ alkenyl or $C_2$-$C_3$ alkynyl group, an alkyl- or halogen-substituted $C_6$-$C_8$ aryl, unsubstituted $C_6$-$C_8$ aryl group or a $C_7$-$C_9$ aralkyl group.

2. 2,3-Dimethylmaleimidomethyl 2', 2'-dimethyl-3'-(2,2-dichlorovinyl)-cyclopropanecarboxylate.

3. 2-Methyl-3-ethylmaleimidomethyl 2', 2'-dimethyl-3'-(2,2-dichlorovinyl)-cyclopropanecarboxylate.

4. 2,3-Diethylmaleimidomethyl 2', 2'-dimethyl-3'-(2,2-difluorovinyl)-cyclopropanecarboxylate.

5. 2,3-Dimethylmaleimidomethyl 2', 2'-dimethyl-3'-(2,2-dibromovinyl)-cyclopropanecarboxylate.

6. 2-Methyl-3-isopropylmaleimidomethyl 2', 2'-dimethyl-3'-(2-chlorovinyl)-cyclopropanecarboxylate.

7. An insecticidal composition comprising an inert carrier and as the active ingredient an insectidally effective amount of a cyclopropanecarboxylic acid ester of the formula (I),

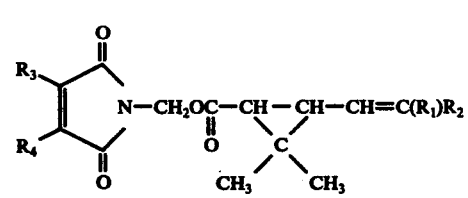

wherein $R_1$ is a hydrogen atom, methyl group or a fluorine, chlorine or bromine atom, $R_2$ is a fluorine, chlorine or bromine atom, and each of $R_3$ and $R_4$ is independently a hydrogen atom, a $C_1$-$C_3$ alkyl, $C_2$-$C_3$ alkenyl or $C_2$-$C_3$ alkynyl group, an alkyl- or halogen-substituted $C_6$-$C_8$ aryl or unsubstituted $C_6$-$C_8$ aryl group or a $C_7$-$C_9$ aralkyl group.

8. A composition according to claim 7, wherein the said composition is in the form of an emulsifiable concentrate, wettable powder, dust, granules, fine granules, oil spray, aerosol, heating fumigant, thermal fogging agent, non-heating fumigant or bait.

9. A method of killing insect or acarid, which comprises applying thereto an insecticidally effective amount of a compound as claimed in claim 1 alone or together with an inert carrier.

* * * * *